(12) United States Patent
Bhardwaj et al.

(10) Patent No.: US 11,961,326 B2
(45) Date of Patent: *Apr. 16, 2024

(54) METHODS AND SYSTEMS FOR MAINTAINING HYGIENIC CONDITIONS IN AUTOMATIC TELLER MACHINES

(71) Applicant: Capital One Services, LLC, McLean, VA (US)

(72) Inventors: Shekhar Bhardwaj, Wilmington, DE (US); Andrew Yocca, New York, NY (US); Kelvin Goodman, Washington, DC (US); Christopher McVay, Henrico, VA (US); Dong Zhang, Sterling, VA (US); Neer Pandya, New York, NY (US)

(73) Assignee: Capital One Services, LLC, McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/180,062

(22) Filed: Mar. 7, 2023

(65) Prior Publication Data

US 2023/0237836 A1 Jul. 27, 2023

Related U.S. Application Data

(63) Continuation of application No. 17/862,501, filed on Jul. 12, 2022, now Pat. No. 11,636,707, which is a
(Continued)

(51) Int. Cl.
*G06V 40/16* (2022.01)
*A61L 2/10* (2006.01)
(Continued)

(52) U.S. Cl.
CPC .............. *G06V 40/165* (2022.01); *A61L 2/10* (2013.01); *A61L 2/24* (2013.01); *G06F 3/14* (2013.01);
(Continued)

(58) Field of Classification Search
CPC .... G06V 40/165; G06V 40/171; G06V 20/10; A61L 2/10; A61L 2/24; G06F 3/14; G06N 3/08; G07F 19/20
See application file for complete search history.

(56) References Cited

U.S. PATENT DOCUMENTS

7,809,163 B2 * 10/2010 Sheu ...................... G06V 40/40
382/118
2017/0352015 A1 * 12/2017 Xu ....................... G06V 40/113
(Continued)

*Primary Examiner* — David Bilodeau
(74) *Attorney, Agent, or Firm* — Perkins Coie LLP (57) ABSTRACT

Methods and systems are described for maintaining hygienic conditions in automatic teller machines by detecting whether or not a user is not in compliance with a hygienic standard. If a user is not in compliance, then the automatic teller machine may execute a hygienic action to cleanse the automatic teller machine. For example, the hygienic action may comprise automatically cleansing the automatic teller machine, disabling the automatic teller machine from service, transmitting a sanitation service request to an automatic teller machine provide, and/or initiating an alternative control scheme (e.g., voice controls, gesture-based controls, etc.) for the automatic teller machine.

20 Claims, 6 Drawing Sheets

Related U.S. Application Data continuation of application No. 16/937,520, filed on Jul. 23, 2020, now Pat. No. 11,430,257.

(51) Int. Cl.
*A61L 2/24* (2006.01)
*G06F 3/14* (2006.01)
*G06N 3/08* (2023.01)
*G06V 20/10* (2022.01)
*G07F 19/00* (2006.01)

(52) U.S. Cl.
CPC .............. *G06N 3/08* (2013.01); *G06V 20/10* (2022.01); *G06V 40/171* (2022.01); *G07F 19/20* (2013.01); *A61L 2202/11* (2013.01); *A61L 2202/14* (2013.01)

(56) References Cited

U.S. PATENT DOCUMENTS

| | | | |
|---|---|---|---|
| 2021/0304537 A1* | 9/2021 | Reed | G06F 18/22 |
| 2021/0322600 A1* | 10/2021 | Altman | B08B 7/0057 |
| 2021/0326579 A1* | 10/2021 | Harris | G06V 40/171 |
| 2021/0390806 A1* | 12/2021 | Duke | G07C 9/37 |
| 2022/0027601 A1* | 1/2022 | Bhardwaj | G06V 20/10 |

* cited by examiner

METHODS AND SYSTEMS FOR MAINTAINING HYGIENIC CONDITIONS IN AUTOMATIC TELLER MACHINES

CROSS REFERENCE TO RELATED APPLICATIONS

This application is a continuation of U.S. patent application Ser. No. 17/862,501, filed on Jul. 12, 2022, which is a continuation of U.S. patent application Ser. No. 16/937,520, filed on Jul. 23, 2020. The content of the foregoing applications is incorporated herein in its entirety by reference.

FIELD OF THE INVENTION

The invention relates to for maintaining hygienic conditions in automatic teller machines.

BACKGROUND

In recent years, there has been an increased focus on maintaining hygienic conditions. This focus has only intensified in view of the COVID-19 pandemic of 2020. Maintaining hygienic conditions is however particularly difficult in situations in which multiple users must use the same device. The problem is further exacerbated if the device requires a user to physically touch the device and stand close to the device. An automatic teller machine is this type of device. In addition to requiring a user to touch the automatic teller machine, users often stand very close to the automatic teller machine for security reasons.

SUMMARY

Methods and systems are described herein for maintaining hygienic conditions in automatic teller machines. More specifically, methods and system are described herein for maintaining hygienic conditions in automatic teller machines by detecting whether or not a user is not in compliance with a hygienic standard. If a user is not in compliance, then the automatic teller machine may execute a hygienic action to cleanse the automatic teller machine. For example, the hygienic action may comprise automatically cleansing the automatic teller machine, disabling the automatic teller machine from service, transmitting a sanitation service request to an automatic teller machine provider, and/or initiating an alternative control scheme (e.g., voice controls, gesture-based controls, etc.) for the automatic teller machine.

To determine whether or not to cleanse the automatic teller machine the systems and methods may capture an image of a user at the automatic teller machine using a camera in the automatic teller machine and process the image using a facial recognition model to identify whether or not the user is wearing a mask. More specifically, the system may use a facial recognition model to identify a nose and a mouth of the user. If the nose and mouth cannot be identified (e.g., because they are covered by a mask), the system determines that the user is user is in compliance with a hygienic standard. For example, by using a facial recognition model to identify the nose and mouth of a user (e.g., as opposed to using a model trained to identify whether or not a user is wearing a mask), the system may determine a user is not in compliance with a hygienic standard if he/she is wearing a mask, but wearing it improperly (e.g., wearing it around his/her neck or otherwise not having it cover the nose and mouth of the user).

Furthermore, by having the image captured by a camera in the automatic teller machine and using a facial recognition model that is trained on images of users at automatic teller machines the accuracy of the identification may be improved. For example, automatic teller machines are outfitted with a camera, and the camera is positioned such that any user of the automatic teller machine is necessarily caught on camera and/or subject to the lighting of the automatic teller machine (e.g., glint detected in the eye of a user based on the light may aid in detecting the eyes of a user). Nonetheless, because of the close range, specialized lighting condition, sharp angle, and/or specialized lens (e.g., wide angle lens) used in the camera of an automatic teller machine, an image of a user at an automatic teller machine may appear distorted. By training the facial recognition model on these images as opposed to stock profile images and/or images caught with conventional cameras, the system may account for the distortions and improve accuracy.

In some aspects, a system and method for maintaining hygienic conditions in automatic teller machines is disclosed. For example, the system may receive a user request to initiate a session with an automatic teller machine. In response to receiving the user request, the system may capture an image of a user at the automatic teller machine. The system may process the image using a facial recognition model to identify a nose and a mouth of the user. In response to identifying the nose or mouth in the image, the system may determine that the user is not in compliance with a hygienic standard and execute a hygienic action to cleanse the automatic teller machine.

Various other aspects, features, and advantages of the invention will be apparent through the detailed description of the invention and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise. Additionally, as used in the specification "a portion," refers to a part of, or the entirety of (i.e., the entire portion), a given item (e.g., data) unless the context clearly dictates otherwise.

DETAILED DESCRIPTION OF THE DRAWINGS

In the following description, for the purposes of explanation, numerous specific details are set forth in order to provide a thorough understanding of the embodiments of the invention. It will be appreciated, however, by those having skill in the art, that the embodiments of the invention may be practiced without these specific details or with an equivalent arrangement. In other cases, well-known structures and devices are shown in block diagram form in order to avoid unnecessarily obscuring the embodiments of the invention. It should also be noted that the methods and systems disclosed herein are also suitable for applications unrelated to source code programming.

Figure 1:
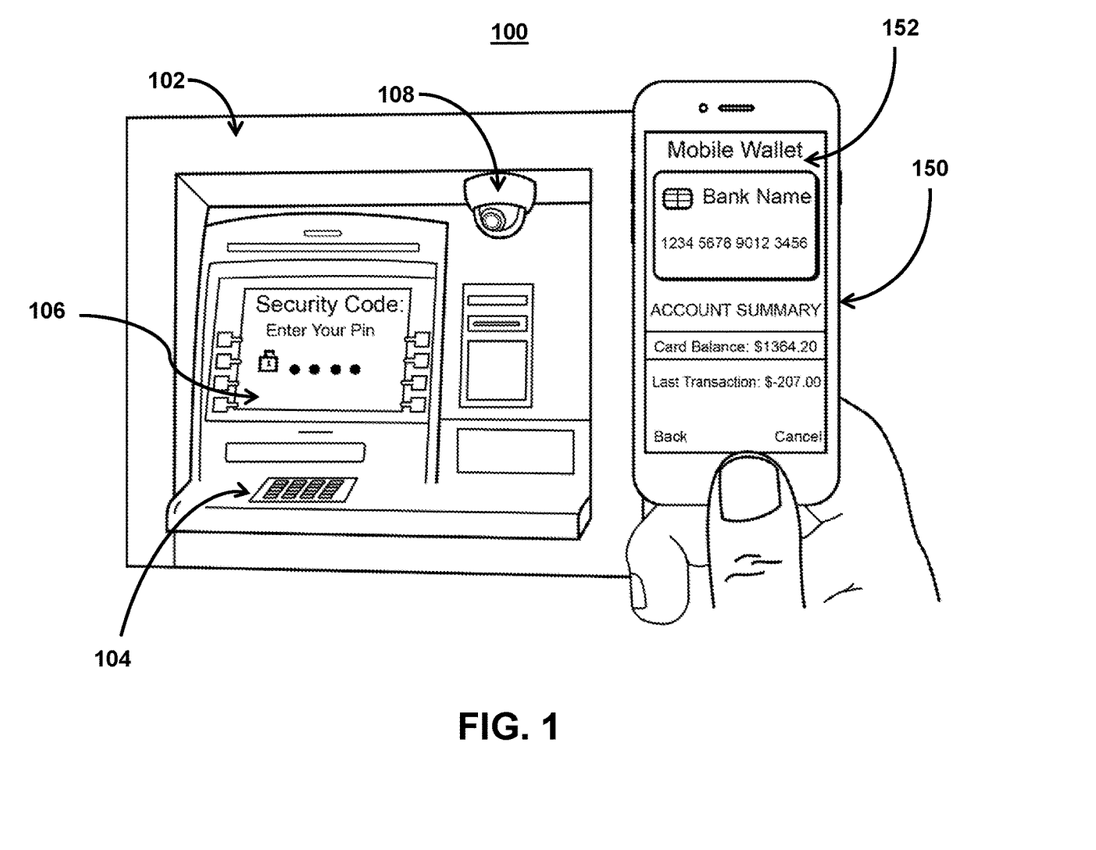
FIG. 1 shows an illustrative system features an automatic teller machine and mobile device, in accordance with one or more embodiments.

FIG. 1 shows an illustrative system featuring an automatic teller machine and mobile device, in accordance with one or more embodiments. For example, FIG. 1 shows system 100. System 100 includes automatic teller machine 102 and secondary device 150. Automatic teller machine 102 may include display 106 whereas secondary device 150 may include display 152. Information used to conduct transactions using system 100 may appear on display 106 and display 152. System 100 may include camera 108, which may be positioned to capture images of a user at the automatic teller machine (e.g., a user using keypad 104).

For example, automatic teller machine 102 may be an electronic banking outlet that allows a user to complete basic transactions without the aid of a branch representative or teller. The automatic teller machine 102 may allow any user with a credit card or debit card to receive cash and/or perform financial actions such as deposits, cash withdrawals, bill payments, and transfers between accounts.

In some embodiments, automatic teller machine 102 and secondary device 150 may initiate a temporary device session in order to perform financial transactions. For example, the temporary device session may be initiated and maintained through the exchange of QR code and/or other image-based and/or electrically communicated codes.

In some embodiments, the automatic teller machine 102 may be self-cleaning. For example, the automatic teller machine 102 may include disinfecting means and/or provide means for disinfecting automatic teller machine 102. For example, the automatic teller machine 102 may generate a notification (e.g., on display 106) asking the user to clean automatic teller machine 102, may automatically clean the automatic teller machine 102, request (e.g., to a provider of the automatic teller machine 102) a cleaning of automatic teller machine 102, and/or disable automatic teller machine 102 until a hygienic standard (e.g., a time limit between users) is compliant.

As referred to herein, a hygienic standard may be defined by hygiene practices related to the administration of medicine and medical care and/or use of the automatic teller machine 102 that prevents or minimizes the spread of disease. In some embodiments, the hygienic standard may be based on respiratory hygiene, which may relate to cover a nose and mouth of a user. In some embodiments, the hygienic standard may be based on the user of protective coverings of a hand and/or face.

Figure 2:
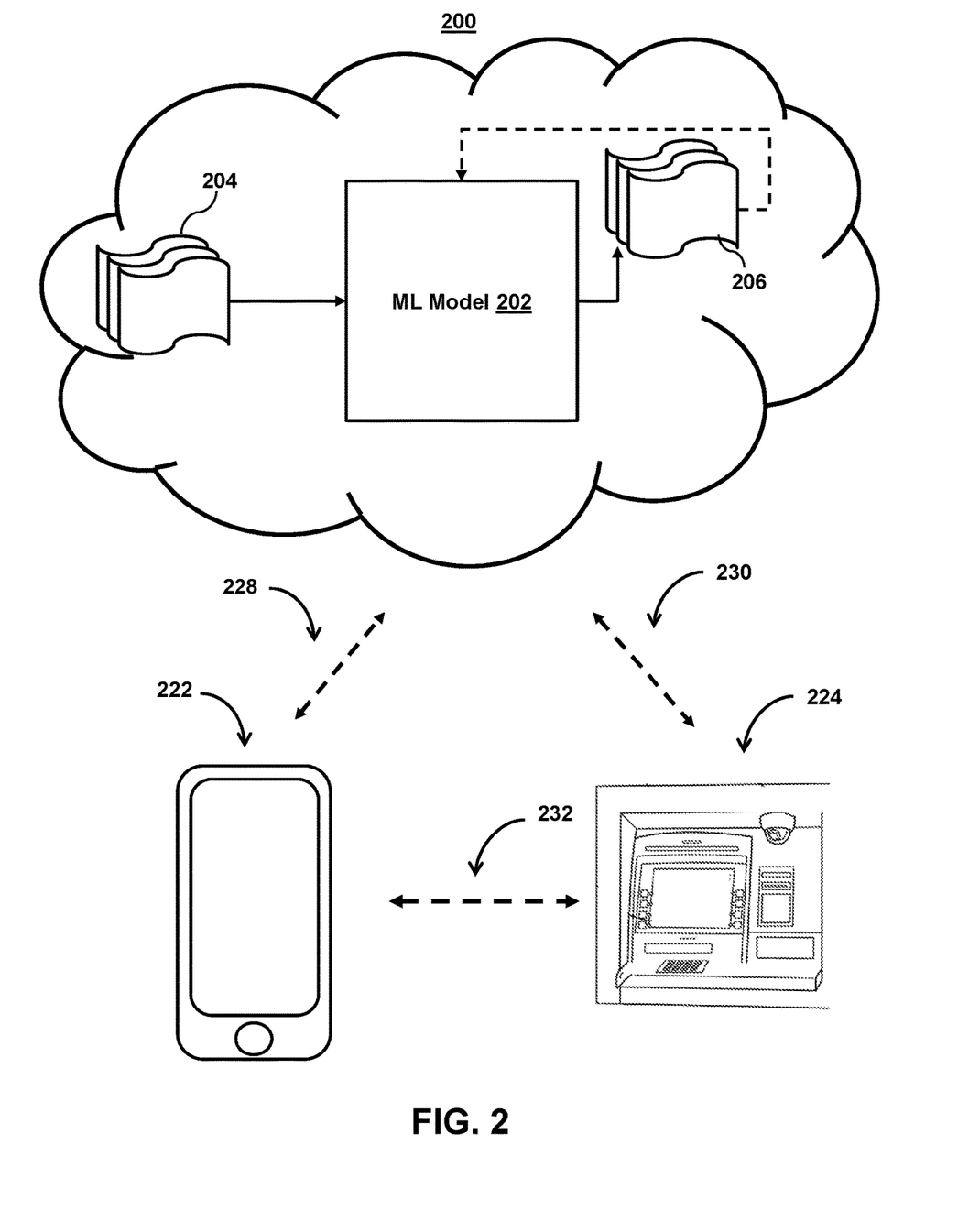
FIG. 2 shows an illustrative system for maintaining hygienic conditions in automatic teller machines, in accordance with one or more embodiments.

FIG. 2 shows an illustrative system for maintaining hygienic conditions in automatic teller machines, in accordance with one or more embodiments. As shown in FIG. 2, system 200 may include user device 222, user device 224, and/or other components. Each user device may include any type of mobile terminal, fixed terminal, or other device. For example, user device 224 may comprise an automatic teller machine (e.g., automatic teller machine 102 (FIG. 1)). For example, each of these devices may comprise one or more of the devices shown in FIG. 1. Each of these devices may receive content and data via input/output (hereinafter "I/O") paths and may also include processors and/or control circuitry to send and receive commands, requests, and other suitable data using the I/O paths. The control circuitry may be comprised of any suitable processing circuitry. Each of these devices may also include a user input interface and/or display for use in receiving and displaying data (e.g., user interface 102 (FIG. 1)).

By way of example, user device 222 may include a desktop computer, a server, or other client device. Users may, for instance, utilize one or more of the user devices to interact with one another, one or more servers, or other components of system 200. It should be noted that, while one or more operations are described herein as being performed by particular components of system 200, those operations may, in some embodiments, be performed by other components of system 200. As an example, while one or more operations are described herein as being performed by components of user device 222, those operations may, in some embodiments, be performed by components of user device 224. System 200 also includes machine learning model 202, which may be implemented on user device 222, user device 224, and/or a cloud-based system, and/or accessible by communication paths 228 and 230, respectively. It should be noted that, although some embodiments are described herein with respect to machine learning models, other prediction models (e.g., statistical models or other analytics models) may be used in lieu of, or in addition to, machine learning models in other embodiments (e.g., a statistical model replacing a machine learning model and a non-statistical model replacing a non-machine learning model in one or more embodiments).

Each of these devices may also include memory in the form of electronic storage. The electronic storage may include non-transitory storage media that electronically stores information. The electronic storage of media may include (i) system storage that is provided integrally (e.g., substantially non-removable) with servers or client devices and/or (ii) removable storage that is removably connectable to the servers or client devices via, for example, a port (e.g., a USB port, a firewire port, etc.) or a drive (e.g., a disk drive, etc.). The electronic storages may include optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include virtual storage resources (e.g., cloud storage, a virtual private network, and/or other virtual storage resources). The electronic storage may store software algorithms, information determined by the processors, information obtained from servers, information obtained from client devices, or other information that enables the functionality as described herein.

FIG. 2 also includes communication paths 228, 230, and 232. Communication paths 228, 230, and 232 may include the Internet, a mobile phone network, a mobile voice or data network (e.g., a 4G or LTE network), a cable network, a public switched telephone network, or other types of communications network or combinations of communications networks. Communication paths 228, 230, and 232 may include one or more communications paths, such as a satellite path, a fiber-optic path, a cable path, a path that supports Internet communications (e.g., IPTV), free-space connections (e.g., for broadcast or other wireless signals), or any other suitable wired or wireless communications path or combination of such paths. The computing devices may include additional communication paths linking a plurality of hardware, software, and/or firmware components operating together. For example, the computing devices may be implemented by a cloud of computing platforms operating together as the computing devices.

As an example, with respect to FIG. 2, machine learning model 202 may take inputs 204 and provide outputs 206. For example, machine learning model 202 may be used by an automatic teller machine (e.g., automatic teller machine 102 (FIG. 1)) and/or a financial services provider to receive, from a user device of a user, a user request to access the automatic teller machine. Machine learning model 202 may then be used by an automatic teller machine (e.g., automatic teller machine 102 (FIG. 1)) to generate for display, on the user device, a recommendation for the location from a subset at which to access the service at a given time interval. For example, machine learning model 202 may be used to efficiently process information on available services, sanitation conditions, and assessments of user compliance with hygienic standards in order to provide real-time recommendations.

The inputs may include multiple data sets such as a training data set and a test data set. In some embodiments, outputs 206 may be fed back to machine learning model 202 as input to train machine learning model 202 (e.g., alone or in conjunction with user indications of the accuracy of outputs 206, labels associated with the inputs, or with other reference feedback information). In another embodiment, machine learning model 202 may update its configurations (e.g., weights, biases, or other parameters) based on the assessment of its prediction (e.g., outputs 206) and reference feedback information (e.g., user indication of accuracy, reference labels, or other information). In another embodiment, where machine learning model 202 is a neural network, connection weights may be adjusted to reconcile differences between the neural network's prediction and the reference feedback. In a further use case, one or more neurons (or nodes) of the neural network may require that their respective errors are sent backward through the neural network to them to facilitate the update process (e.g., backpropagation of error). Updates to the connection weights may, for example, be reflective of the magnitude of error propagated backward after a forward pass has been completed. In this way, for example, the machine learning model 202 may be trained to generate better predictions.

In some embodiments, machine learning model 202 may include an artificial neural network. In such embodiments, machine learning model 202 may include an input layer and one or more hidden layers. Each neural unit of machine learning model 202 may be connected with many other neural units of machine learning model 202. Such connections can be enforcing or inhibitory in their effect on the activation state of connected neural units. In some embodiments, each individual neural unit may have a summation function which combines the values of all of its inputs together. In some embodiments, each connection (or the neural unit itself) may have a threshold function such that the signal must surpass before it propagates to other neural units. Machine learning model 202 may be self-learning and trained, rather than explicitly programmed, and can perform significantly better in certain areas of problem solving, as compared to traditional computer programs. During training, an output layer of machine learning model 202 may correspond to a classification of machine learning model 202 and an input known to correspond to that classification may be input into an input layer of machine learning model 202 during training. During testing, an input without a known classification (e.g., whether or not a user is wearing a mask, whether or not the nose or mouth of a user is identified, and/or a degree to which a hygienic condition is complied with) may be input into the input layer, and a determined classification may be output.

In some embodiments, machine learning model 202 may include multiple layers (e.g., where a signal path traverses from front layers to back layers). In some embodiments, back propagation techniques may be utilized by machine learning model 202 where forward stimulation is used to reset weights on the "front" neural units. In some embodiments, stimulation and inhibition for machine learning model 202 may be more free-flowing, with connections interacting in a more chaotic and complex fashion. During testing, an output layer of machine learning model 202 may indicate whether or not a given input corresponds to a classification of machine learning model 202).

Figure 3:
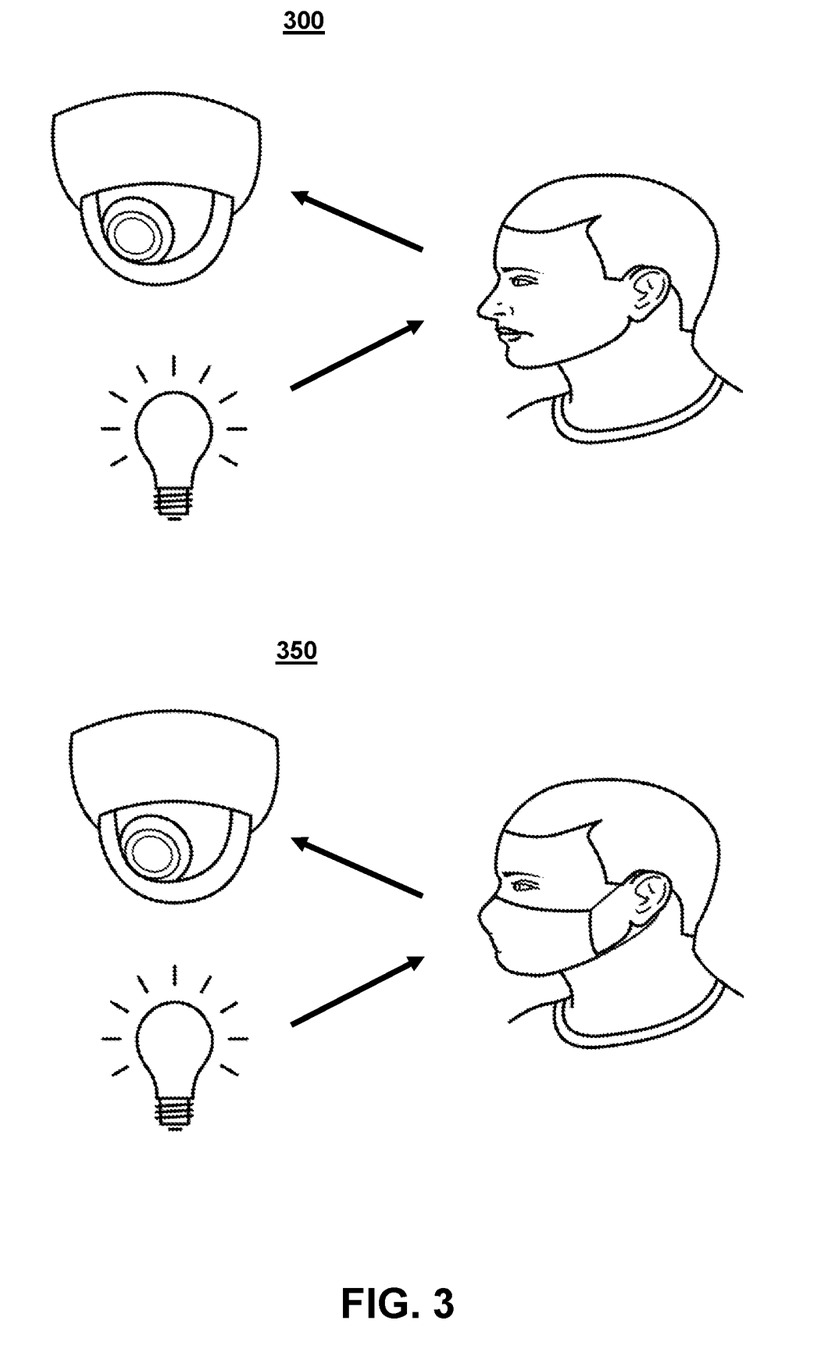
FIG. 3 shows an illustrative system for detecting whether or not a user is in compliance with a hygienic standard in automatic teller machines, in accordance with one or more embodiments.

FIG. 3 shows an illustrative system for detecting whether or not a user is in compliance with a hygienic standard in automatic teller machines, in accordance with one or more embodiments. FIG. 3 shows automatic teller machine camera system 300 and automatic teller machine camera system 350, which may be used to identify whether or not a user is in compliance with a hygienic standard. Automatic teller machine camera system 300 and automatic teller machine camera system 350 may include automatic teller machine control circuitry, an automatic teller machine light source, and an automatic teller machine camera. Automatic teller machine light source transmits light that reaches at least one eye of a user, and automatic teller machine camera is directed at the user to sense reflected light. Automatic teller machine camera may transmit collected data to automatic teller machine control circuitry and based on the data received from automatic teller machine camera, automatic teller machine control circuitry may identify whether or not a user is in compliance with hygienic standards. For example, automatic teller machine camera system 300 may illustrate an example where a user is in compliance with a hygienic standard. Automatic teller machine camera system 350 may illustrate an example where a user is in compliance with a hygienic standard.

In some embodiments, automatic teller machine camera system 300 is configured for identifying facial features of a user. For example, the system may identify a facial feature and a distance between facial features. Furthermore, automatic teller machine control circuitry may be integrated with one or more automatic teller machine light sources and one or more automatic teller machine cameras in order to generate images specific to users using automatic teller machines. Additionally or alternatively, one or more automatic teller machine light sources and one or more automatic teller machine cameras may be housed separately from automatic teller machine control circuitry and in wireless or wired communication with automatic teller machine control circuitry.

Automatic teller machine light source transmits light to one or both eyes of one or more users. Automatic teller machine light source may emit, for example, infrared (IR) light, near infrared light, or visible light. The light emitted by automatic teller machine light source may be collimated or non-collimated. The light is reflected in a user's eye, forming, for example, the reflection from the outer surface of the cornea (i.e., a first Purkinje image), the reflection from the inner surface of the cornea (i.e., a second Purkinje image), the reflection from the outer (anterior) surface of the lens (i.e., a third Purkinje image), and/or the reflection from the inner (posterior) surface of the lens (i.e., a fourth Purkinje image). Moreover, an automatic teller machine camera may be configured to capture images based on the specialized light source of the automatic teller machine.

Automatic teller machine camera collects visual information, such as an image or series of images, of one or both of one or more users' eyes. Automatic teller machine camera transmits the collected image(s) to automatic teller machine control circuitry, which processes the received image(s) to identify a glint (i.e., corneal reflection) and/or other reflection in one or both eyes of one or more users. Automatic teller machine control circuitry may also determine the location of the center of the pupil of one or both eyes of one or more users. For each eye, automatic teller machine control circuitry may compare the location of the pupil to the location of the glint and/or other reflection to estimate the gaze point. Automatic teller machine control circuitry may also store or obtain information describing the location of one or more automatic teller machine light sources and/or the location of one or more automatic teller machine cameras relative to a display (e.g., display 106 (FIG. 1)). Using this information, automatic teller machine control circuitry may determine a likely position of a user's eyes based on the glint. Once the system determines a position of the user's eyes, the system may attempt to identify other facial features (e.g., a nose and a mouth).

In some embodiments, automatic teller machine camera system 300 is configured to account for a user's head movement and/or the position of a user's head while using the automatic teller machine. In some embodiments accounting for a user's head position, automatic teller machine camera system 300 includes two or more automatic teller machine cameras. For example, two cameras may be arranged to form a stereo vision system for obtaining a 3D position of the user's eye or eyes. Furthermore, multiple cameras may allow the automatic teller machine control circuitry to compensate for head movement when determining the user's gaze point. The two or more automatic teller machine cameras may be part of a single unit or may be separate units. For example, an automatic teller machine camera system 300 in communication with the user device (e.g., user device 222 (FIG. 2)) may include two automatic teller machine cameras. In other embodiments, each user device (e.g., user device 222 (FIG. 2)) and automatic teller machine camera system 300 may include an optical sensor, and automatic teller machine control circuitry receives image data from the optical sensor of the user device and the optical sensor of automatic teller machine camera system 300.

In other embodiments accounting for a user's head movement, automatic teller machine camera system 300 includes two or more light sources for generating multiple glints. For example, two automatic teller machine light sources may create glints at different locations of an eye. Automatic teller machine control circuitry may also receive data identifying the location of automatic teller machine light sources relative to a display (e.g., display 106 (FIG. 1)) and/or adjust an automatic teller machine camera system 300.

Figure 4:
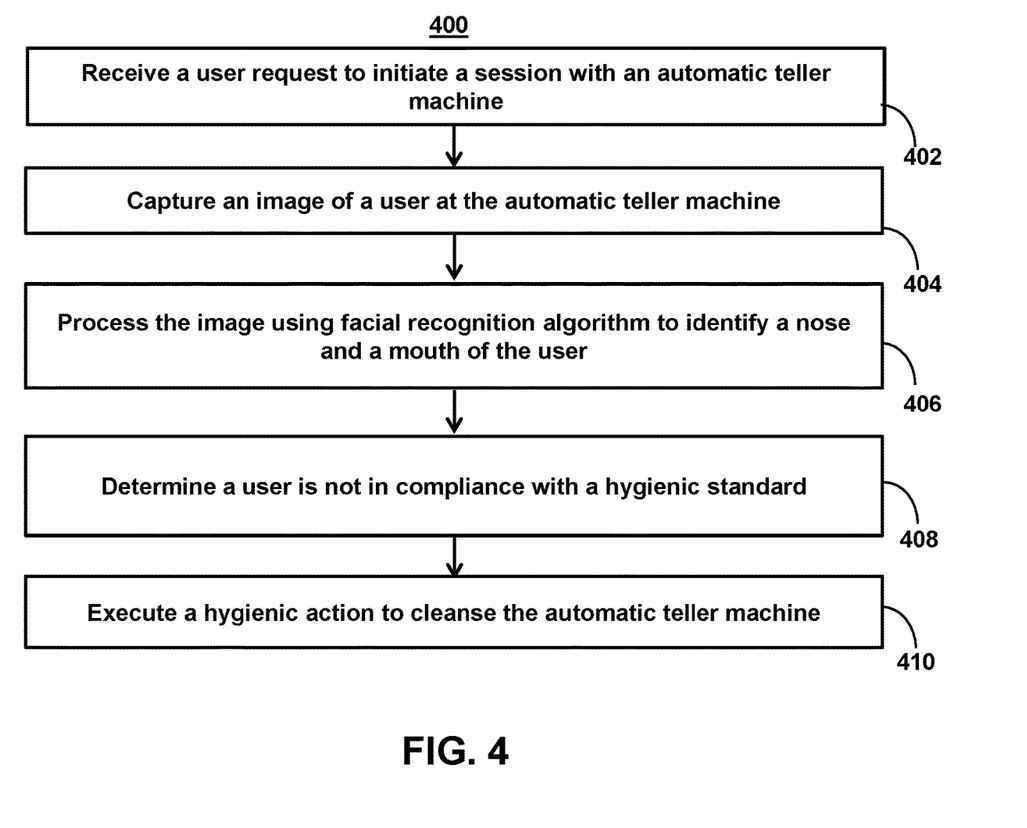
FIG. 4 shows a flowchart of the steps involved in maintaining hygienic conditions in automatic teller machines, in accordance with one or more embodiments.

FIG. 4 shows a flowchart of the steps involved in maintaining hygienic conditions in automatic teller machines, in accordance with one or more embodiments. In some embodiments, process 400 may be performed by one or more components of the systems shown in FIGS. 1-3.

At step 402, process 400 receives (e.g., via one or more components of FIGS. 1-2) a user request to initiate a session with an automatic teller machine. For example, the system may receive a user request (e.g., via inputs to the automatic teller machine, based on the automatic teller machine detecting a user's approach, etc.) to initiate a session with an automatic teller machine. For example, the system may, in response to receiving the user request, verify an identify of user at the automatic teller machine. The system may determine a user account associated with the user. In response to determining a user account (e.g., a bank account number of other number associated with a financial services provider and/or the automatic teller machine).

At step 404, process 400 captures (e.g., via one or more components of FIGS. 1-2) an image of a user at the automatic teller machine. For example, the system may capture an image of a user at the automatic teller machine in response to receiving the user request. For example, as described in FIG. 3, the system may capture an image of the user at the automatic teller machine using a camera in the automatic teller machine. For example, automatic teller machines are outfitted with a camera, and the camera is positioned such that any user of the automatic teller machine is necessarily caught on camera and/or subject to the lighting of the automatic teller machine (e.g., glint detected in the eye of a used based on the light may aid in detecting the eyes of a user).

At step 406, process 400 processes (e.g., via one or more components of FIGS. 1-2) the image using facial recognition algorithm to identify a nose and a mouth of the user. For example, the system may process the image using facial recognition model to identify a nose and a mouth of the user. For example, the facial recognition model (as described in FIG. 2 above) may comprise a machine learning model trained to identify noses and faces in images. For example, the machine learning model is further trained to identify whether users are wearing masks (e.g., based on the noses and faces in images). Furthermore, by training the facial recognition model on these images as opposed to stock profile images and/or images caught with conventional cameras, the system may account for the distortions in the images as a result of the camera and improve accuracy.

At step 408, process 400 determines (e.g., via one or more components of FIGS. 1-2) a user is not in compliance with a hygienic standard. For example, the system may, in response to identifying the nose or mouth in the image, determine that the user is not in compliance with a hygienic standard. For example, the system may detect eye glint of a user (e.g., as described in FIG. 3), nose, and/or other facial features of a user. In some embodiments, the system may determine a degree of compliance with the hygienic standard and/or select a hygienic action based on the degree of compliance.

At step 410, process 400 executes (e.g., via one or more components of FIGS. 1-2) a hygienic action to cleanse the automatic teller machine. For example, the system may, in response to identifying the nose or mouth in the image, execute a hygienic action to cleanse the automatic teller machine. In contrast, in response to not identifying the nose or mouth in the image, the system may determine that the user is in compliance with the hygienic standard.

For example, the hygienic action may comprise initiating an ultraviolet sanitation procedure on the automatic teller machine. For example, the automatic teller machine may include an ultraviolet germicidal irradiation device incorporated into the automatic teller machine. The device may use short-wavelength ultraviolet (ultraviolet C or UV-C) light to kill or inactivate microorganisms by destroying nucleic acids and disrupting their DNA, leaving them unable to perform vital cellular functions. In some embodiments, the device may be a mercury-vapor lamp that has a strong emission line at 254-290 nm, which is within the range of wavelengths that demonstrate strong disinfection effect.

Additionally or alternatively, the hygienic action comprises disabling the automatic teller machine from service and/or generating for display, on a display screen of the automatic teller machine, a notification to use an alternative automatic teller machine. For example, the system may generate a notification that may include directions to another automatic teller machine and/or a time when the automatic teller machine with be sanitized and/or enabled. For example, the hygienic action may comprise of transmitting a sanitation service request to an automatic teller machine provider and/or the automatic teller machine may remain disabled until the automatic teller machine is sanitized.

It is contemplated that the steps or descriptions of FIG. 4 may be used with any other embodiment of this disclosure. In addition, the steps and descriptions described in relation to FIG. 4 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 1-3 could be used to perform one or more of the steps in FIG. 4

Figure 5:
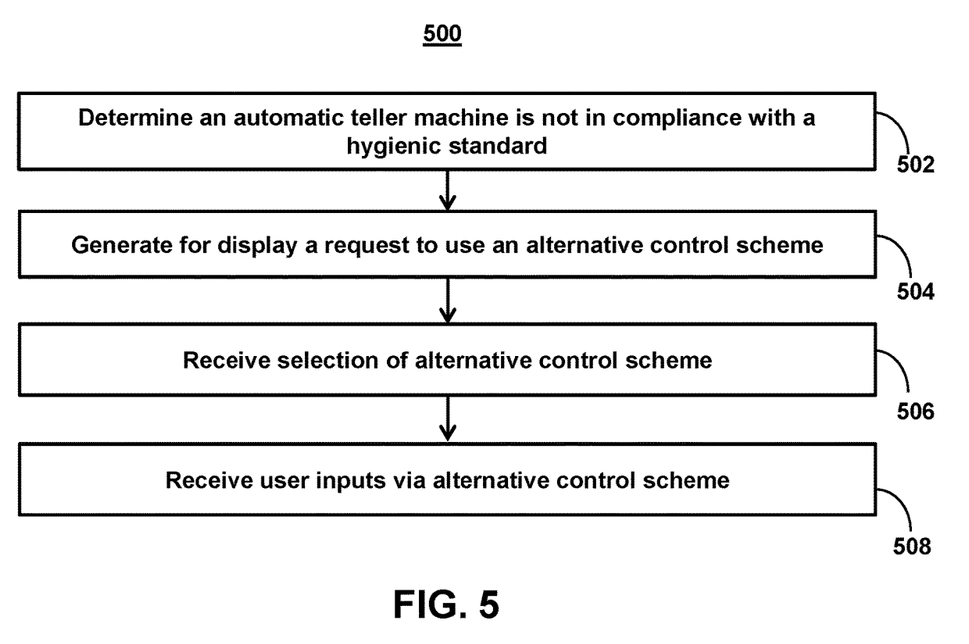
FIG. 5 shows a flowchart of the steps involved in implementing an alternative control scheme in response to determining a user is not in compliance with a hygienic standard, in accordance with one or more embodiments.

FIG. 5 shows a flowchart of the steps involved in implementing an alternative control scheme in response to determining a user is not in compliance with a hygienic standard, in accordance with one or more embodiments. In some embodiments, process 500 may be performed by one or more components of the systems shown in FIGS. 1-3.

At step 502, process 500 determines (e.g., via one or more components of FIGS. 1-2) an automatic teller machine is not in compliance with a hygienic standard. For example, the system may determine that a user is not wearing a mask (e.g., the system may identify a nose or mouth in an image of a user at an automatic teller machine.

At step 504, process 500 generates (e.g., via one or more components of FIGS. 1-2) for display a request to use an alternative control scheme. For example, the system may execute a hygienic action in response to determining a user is not wearing a mask. In some embodiments, the alternative control scheme may comprise gesture-based control or voice activated controls. For example, the system may display (or present via an audio output) a request to user gesture-based control or a voice activated controls. In some embodiments, the alternative control scheme may comprise controlling the automatic teller machine via a secondary device. For example, the system may display (on a user interface of the secondary device) a request to use the secondary device to control the automatic teller machine. Additionally, the system may issue a pairing request with the secondary device and/or initiate another device session between the automatic teller machine and the secondary device.

At step 506, process 500 receives (e.g., via one or more components of FIGS. 1-2) selection of alternative control scheme. For example, the hygienic action may comprise initiating an alternative control scheme for the automatic teller machine. In some embodiments, the alternative control scheme may comprise gesture-based control or voice activated controls. For example, the system may capture a gesture from a user and/or receive a voice command from the user and in response the system may select the alternative control scheme. In some embodiments, the alternative control scheme may comprise controlling the automatic teller machine via a secondary device. For example, the system may receive a control command or acceptance of the alternative control scheme from the secondary device.

At step 508, process 500 receives (e.g., via one or more components of FIGS. 1-2) user inputs via alternative control scheme. For example, the system may continue to receive user inputs using the selected alternative control scheme. For example, for gesture-based controls, the camera of the automatic teller machine may be a depth-aware camera that generates a depth map of what is being seen through the camera at a short range, and use this data to approximate a three dimension representation of what is being seen. These can be effective for detection of hand gestures due to their short range capabilities such as American signal language gestures and/or other hand gestures. In some embodiments, the system may include multiple cameras that detect three dimensional relationships to the images created by the multiple cameras. In some embodiments, the system may also use one or more three dimensional model-based algorithms.

It is contemplated that the steps or descriptions of FIG. 5 may be used with any other embodiment of this disclosure. In addition, the steps and descriptions described in relation to FIG. 5 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 1-3 could be used to perform one or more of the steps in FIG. 5.

Figure 6:
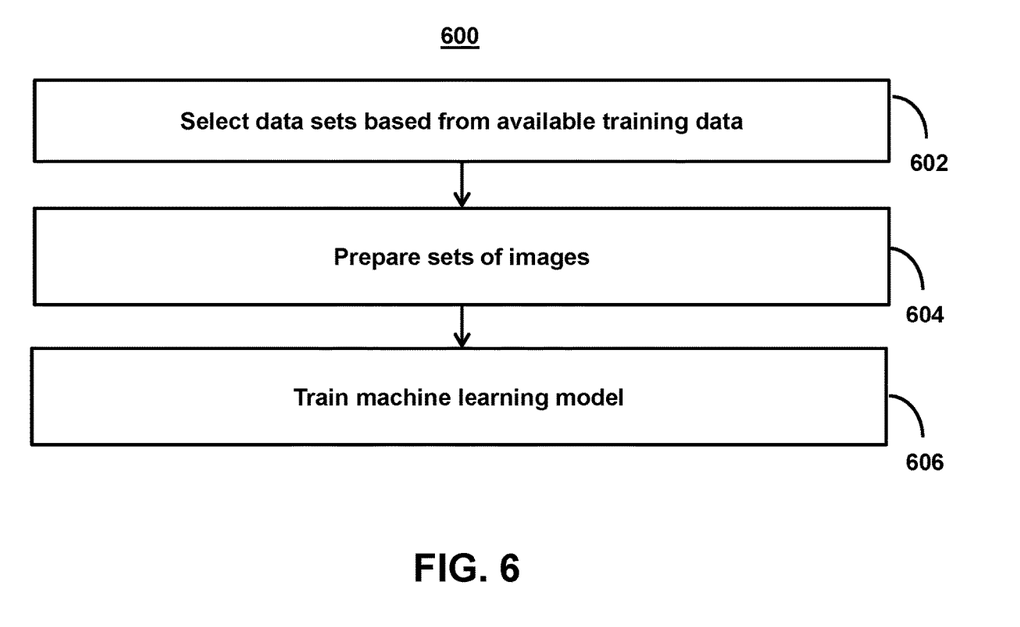
FIG. 6 shows a flowchart of the steps involved in training a machine learning model to determine whether or not a user is in compliance with a hygienic standard, in accordance with one or more embodiments.

FIG. 6 shows a flowchart of the steps involved in training a machine learning model (e.g., machine learning model 202 (FIG. 2)) to determine whether or not a user is in compliance with a hygienic standard, in accordance with one or more embodiments. For example, FIG. 6 describes process 600 for determining whether or not a user of an automatic teller machine is wearing a mask.

At step 602, process 600 selects data sets from available training data. For example, the system may be trained based on images of users at an automatic teller machine. By training the machine learning model on these images as opposed to stock profile images and/or images caught with conventional cameras, the system may account for any distortions attributable to the close range, specialized lighting conditions, sharp angles, and/or specialized lens (e.g., wide angle lens) used in a camera of an automatic teller machine—thus improving accuracy.

At step 604, process 600 prepares sets of images. For example, the system may prepare the data for training the machine learning model. For example, the system may randomize a first training characteristic (e.g., a given lighting condition) or control for the first training characteristic. For example, the first training characteristic may be a setting or characteristic specific to a camera used to capture the first training set of images.

At step 606, process 600 trains a machine learning model using a first training set of images comprising users at automatic teller machine with corresponding labels for a trait (e.g., whether a nose or mouth is present, whether a user is wearing gloves, whether or not a user is wearing a mask, etc.). The system may train the machine learning model to detect one or more traits, which may include any characteristic that may distinguish one classification from another.

In some embodiments, the machine learning model may be a convolutional neural network. The convolutional neural network is an artificial neural network that features one or more convolutional layers. Convolution layers extract features from an input image. Convolution preserves the relationship between pixels by learning image features using small squares of input data. For example, the relationship between the individual parts of a face of a user (e.g., eyes, nose, moth, etc.) may be preserved. In another example, the relationship between a glint of an eye (e.g., as discussed in FIG. 3) may be preserved to identify an eye of a user and its relationship to other facial features of the user.

It is contemplated that the steps or descriptions of FIG. 6 may be used with any other embodiment of this disclosure. In addition, the steps and descriptions described in relation to FIG. 6 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 1-3 could be used to perform one or more of the steps in FIG. 6.

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

The present techniques will be better understood with reference to the following enumerated embodiments:

1. A method for maintaining hygienic conditions in automatic teller machines, the method comprising: receiving a user request to initiate a session with an automatic teller machine; in response to receiving the user request, capturing an image of a user at the automatic teller machine; processing the image using a facial recognition model to identify a nose and a mouth of the user; in response to identifying the nose or mouth in the image: determining that the user is not in compliance with a hygienic standard; and executing a hygienic action to cleanse the automatic teller machine.

2. The method of embodiment 1, wherein the hygienic action comprises initiating an ultraviolet sanitation procedure on the automatic teller machine.

3. The method of any of the preceding embodiments, wherein the hygienic action comprises generating for display, on a display screen of the automatic teller machine, a notification to use an alternative automatic teller machine.

4. The method of any of the preceding embodiments, wherein the hygienic action comprises disabling the automatic teller machine from service.

5. The method of any of the preceding embodiments, wherein the hygienic action comprises transmitting a sanitation service request to an automatic teller machine provider.

6. The method of any of the preceding embodiments, wherein the hygienic action comprises initiating an alternative control scheme for the automatic teller machine, and wherein the alternative control scheme comprises gesture-based control or voice activated controls.

7. The method of any of the preceding embodiments, wherein the hygienic action comprises initiating an alternative control scheme for the automatic teller machine, and wherein initiating the alternative control scheme comprises: generating for display, on a display screen of the automatic teller machine, a request to user a secondary input device; initiating a device session with the secondary device; and receiving user inputs via the secondary device.

8. The method of any of the preceding embodiments, further comprising: in response to receiving the user request, verifying an identify of user at the automatic teller machine; and determining a user account associated with the user.

9. The method of any of the preceding embodiments, wherein the facial recognition model comprises a machine learning model trained to identify noses and faces in images.

10. The method of embodiment 9, wherein the machine learning model is further trained to identify whether users are wearing masks.

11. The method of any of the preceding embodiments further comprising determining that the user is in compliance with the hygienic standard in response to not identifying the nose or mouth in the image.

11. A tangible, non-transitory, machine-readable medium storing instructions that, when executed by a data processing apparatus, cause the data processing apparatus to perform operations comprising those of any of embodiments 1-10.

12. A system comprising: one or more processors; and memory storing instructions that, when executed by the processors, cause the processors to effectuate operations comprising those of any of embodiments 1-10.

13. A system comprising means for performing any of embodiments 1-10.

What is claimed is:

1. A system for maintaining hygienic conditions in automatic teller machines based on images of users of the automatic teller machines, the system comprising:
   an automatic teller machine;
   a camera at the automatic teller machine configured to capture images of users; and
   control circuitry configured to:
      receive a user request to initiate a session with an automatic teller machine;
      verify an identify of user at the automatic teller machine in response to receiving the user request;
      capture an image of a user at the automatic teller machine using the camera;
      process the image using facial recognition model, wherein the facial recognition model is trained based on images of users at an automatic teller machine;
      determine, based on an output of the facial recognition model, that the user is not in compliance with a hygienic standard; and
      execute a hygienic action to cleanse the automatic teller machine.

2. A method for maintaining hygienic conditions in automatic teller machines based on images of users of the automatic teller machines, the method comprising:
   receiving a user request to initiate a session with an automatic teller machine;
   in response to receiving the user request, capturing an image of a user at the automatic teller machine;
   processing the image using a facial recognition model;
   determining, based on an output of the facial recognition model, that the user is not in compliance with a hygienic standard; and
   executing a hygienic action to cleanse the automatic teller machine.

3. The method of claim 2, further comprising determining that the user is in compliance with the hygienic standard in response to not identifying a facial feature in the image.

4. The method of claim 2, wherein the hygienic action comprises generating for display, on a display screen of the automatic teller machine, a notification to use an alternative automatic teller machine.

5. The method of claim 2, wherein the hygienic action comprises disabling the automatic teller machine from service.

6. The method of claim 2, wherein the hygienic action comprises transmitting a sanitation service request to an automatic teller machine provider.

7. The method of claim 2, wherein the hygienic action comprises initiating an alternative control scheme for the automatic teller machine, and wherein the alternative control scheme comprises gesture-based control or voice activated controls.

8. The method of claim 2, wherein the hygienic action comprises initiating an alternative control scheme for the automatic teller machine, and wherein initiating the alternative control scheme comprises:
generating for display, on a display screen of the automatic teller machine, a request to use a secondary input device;
initiating a device session with the secondary device; and
receiving user inputs via the secondary device.

9. The method of claim 2, further comprising:
in response to receiving the user request, verifying an identify of user at the automatic teller machine; and
determining a user account associated with the user.

10. The method of claim 2, wherein the facial recognition model comprises a machine learning model trained to identify noses or faces in images.

11. The method of claim 10, wherein the machine learning model is further trained to identify whether users are wearing masks.

12. A non-transitory computer-readable media comprising instructions that, when executed by one or more processors, cause operations comprising:
receiving a user request to initiate a session with an automatic teller machine;
capturing an image of a user at the automatic teller machine in response to receiving the user request;
processing the image using facial recognition technology;
determining that the user is not in compliance with a standard; and
executing an action at the automatic teller machine.

13. The non-transitory computer-readable media of claim 12, wherein the instructions further cause operations comprising determining that the user is in compliance with the standard in response to not identifying a facial feature in the image.

14. The non-transitory computer-readable media of claim 12, wherein the action comprises generating for display, on a display screen of the automatic teller machine, a notification to use an alternative automatic teller machine.

15. The non-transitory computer-readable media of claim 12, wherein the action comprises disabling the automatic teller machine from service.

16. The non-transitory computer-readable media of claim 12, wherein the action comprises transmitting a sanitation service request to an automatic teller machine provider.

17. The non-transitory computer-readable media of claim 12, wherein the action comprises initiating an alternative control scheme for the automatic teller machine, and wherein the alternative control scheme comprises gesture-based control or voice activated controls.

18. The non-transitory computer-readable media of claim 12, wherein the action comprises initiating an alternative control scheme for the automatic teller machine, and wherein initiating the alternative control scheme comprises:
generating for display, on a display screen of the automatic teller machine, a request to use a secondary input device;
initiating a device session with the secondary device; and
receiving user inputs via the secondary device.

19. The non-transitory computer-readable media of claim 12, wherein the instructions further cause operations comprising:
in response to receiving the user request, verifying an identify of user at the automatic teller machine; and
determining a user account associated with the user.

20. The non-transitory computer-readable media of claim 12, wherein the facial recognition technology comprises a machine learning model trained to identify noses or faces in images.

* * * * *